United States Patent [19]

Corring

[11] Patent Number: 4,836,948

[45] Date of Patent: Jun. 6, 1989

[54] VISCOELASTIC GEL DETERGENT COMPOSITIONS

[75] Inventor: Robert Corring, Rockaway Township, Delaware County, N.J.

[73] Assignee: Lever Brothers Company, New York, N.Y.

[21] Appl. No.: 139,490

[22] Filed: Dec. 30, 1987

[51] Int. Cl.$^4$ .................. C11D 3/12; C11D 3/37; C11D 17/08

[52] U.S. Cl. ..................... 252/99; 252/140; 252/173; 252/174.21; 252/174.24; 252/174.25

[58] Field of Search ............. 252/99, 140, 174.21, 252/174.24, 174.25, DIG. 14, 173

[56] References Cited

U.S. PATENT DOCUMENTS

| | | | |
|---|---|---|---|
| 2,798,053 | 7/1957 | Brown | 260/2.2 |
| 3,060,124 | 10/1962 | Ginn | 252/135 |
| 3,558,496 | 1/1971 | Zmoda | 252/95 |
| 3,579,455 | 4/1971 | Sabatelli et al. | 252/135 |
| 3,609,102 | 9/1971 | Schlossman | 252/522 |
| 3,720,621 | 3/1973 | Smeets | 252/135 |
| 3,896,056 | 7/1975 | Benjamin et al. | 252/539 |
| 3,898,186 | 8/1975 | Mermelstein et al. | 252/528 |
| 4,116,849 | 9/1978 | Leikhim | 252/103 |
| 4,130,501 | 12/1974 | Lutz et al. | 252/186 |
| 4,215,004 | 7/1980 | Borgerding et al. | 252/156 |
| 4,226,736 | 10/1980 | Bush et al. | 252/135 |
| 4,228,048 | 10/1980 | Tesdahl | 260/17.4 |
| 4,260,528 | 4/1981 | Fox et al. | 252/525 |
| 4,431,559 | 2/1984 | Ulrich | 252/99 |
| 4,464,281 | 8/1984 | Rapisarda | 252/174.21 |
| 4,511,487 | 4/1985 | Pruhs et al. | 252/99 |
| 4,512,908 | 4/1985 | Heile | 252/160 |
| 4,762,637 | 8/1988 | Aronson | 252/99 |

FOREIGN PATENT DOCUMENTS

| | | |
|---|---|---|
| 59-36198 | 2/1984 | Japan . |
| 59-36200 | 2/1984 | Japan . |
| 2116199 | 9/1983 | United Kingdom . |
| 2140450 | 11/1984 | United Kingdom . |
| 2163447 | 2/1986 | United Kingdom . |
| 2163448 | 2/1986 | United Kingdom . |
| 2164350 | 3/1986 | United Kingdom . |
| 2176495 | 12/1986 | United Kingdom . |
| 8303621 | 10/1983 | World Int. Prop. O. . |

OTHER PUBLICATIONS

J. Ferry, "Viscoelastic Properties of Polymers", Third Edition, John Wiley & Sons, New York 1980.

Akkerman, J. "A Cross-Linking Mechanism of Polyacrylates with Aluminum Compounds", Congr. FATIPEC, 1984, 17 (3), 155–73.

Greenburg, A. and Qckusy, R., "Dynamic Properties of Cross-Linked Poly(acrylic acid)—Aluminum Oxide Composites", J. Mater. Sci., 1980 15 (12), 3159–62.

B. F. Goodrich Technical Bulletin on Carbopol.

*Primary Examiner*—Dennis Albrecht
*Attorney, Agent, or Firm*—Milton L. Honig

[57] ABSTRACT

A cleaning composition is provided in gel form having a viscosity on a Haake Rotovisco RV-100 Viscometer at 25° C. under 5 sec$^{-1}$ shear of from about 1,000 to 20,000 cps and under 21 sec$^{-1}$ shear of from about 200 to 5,000 cps, a pH range from 11 to 13, and a steady state viscoelastic deformation compliance $J_e°$ greater than 0.01. In one embodiment, the composition comprises a polycarboxylate polymeric thickener, especially a cross-linked polyacrylic acid. There preferably is also present a trivalent metal containing material, especially an aluminum containing material such as alumina. A structuring chelant is a further preferred component which is selected from the salts of carbonate, pyrophosphate and mixtures thereof. When mixed with the polycarboxylate polymer and trivalent metal material, the structuring chelant can form a clear gel.

24 Claims, No Drawings

VISCOELASTIC GEL DETERGENT COMPOSITIONS

BACKGROUND OF THE INVENTION

1. Field of the Invention

The invention relates to a detergent composition in gel form useful for a wide variety of cleaning purposes and of special application for cleaning dishes in an automatic dishwasher.

2. The Prior Art

Automatic dishwashing detergents for home use have traditionally been in powder or granulate form. More recently, the marketplace has seen the advent of liquid forms of automatic dishwashing products. Liquids have advantages over powders in their convenience of dispensing or dosing, their enhanced solubility, absence of lump formation or "caking" during storage, and absence of dustiness associated with the powder form.

Since automatic dishwashing machines contain a dispenser cup normally intended for powders, chemists have been challenged in formulating a liquid product of appropriate rheological properties.

Firstly, the composition must be a uniform mixture to deliver an optimum combination of active ingredients to the wash with each dose. Thus, the liquid must possess physical stability against syneresis or physical separation of its active components during storage.

Secondly, a liquid product must be compatible with automatic dishwashing equipment presently available to the consumer. Home dishwashers are fitted with a closed cup to house detergent through several cycles preliminary to the wash cycle. Cups in these machines do not seal tightly and do not adequately retain liquids of low viscosity. Excessive leakage leads to underdosing in the wash cycle. Performance may be adversely affected. Consequently, any liquid product must possess high viscosity to be effectively retained in the cup and avoid leakage into cycles preceding that of the wash.

Conversely, there are situations where the product should have low viscosity. A low viscosity is desirable for easy dispensing of product from its bottle. Thixotropic liquids address the foregoing dilemma by maintaining high viscosity for storage but reverting to lower viscosity under influence of applied shear. Thixotropy is shear thinning behavior that is time dependent in both its decrease in viscosity under applied shear and its regain of viscosity after cessation of shearing.

The earliest approaches to these problems involved the use of clays to modify viscosity. Typical of this technology are the compositions disclosed in U.S. Pat. Nos. 4,116,849 (Leikhim), 4,431,559 (Ulrich), GB Nos. 2 116 199A (Julemont et al.) and 2 140 450A (Julemont et al.). Some patents such as U.S. Pat. Nos. 4,511,487 (Pruhs et al.) and 4,512,908 (Heile) have singled out hectorite as a particularly efficient thickener. There has also been reported in U.S. Pat. No. 3,558,496 (Zmoda) the advantage of combining a negatively charged clay such as hectorite with a positively charged clay such as alumina clay.

GB No. 2 176 495A suggests the use of polyvalent metal salts of long chain fatty acids, such as aluminum or zinc stearate, as stabilizers against phase separation in a clay laiden liquid composition. Another method of improving phase stability in thixotropic liquids is reported in GB No. 2 163 448A. This patent suggests inclusion of a limited amount of a water-soluble potassium salt to achieve a potassium:sodium weight ratio of about 0.04 to 0.5. Relatively large crystals are said to be inhibited from forming when potassium is present thereby resulting in greater stability against separation on ageing. U.S. Pat. No. 3,720,621 (Smeets) reports a further useful property of including some potassium salt within a sodium tripolyphosphate liquid composition. Here the presence of potassium allows the amount of sodium tripolyphosphate included within the aqueous detergent to attain a considerably higher solubility than found in the absence of potassium.

Although generally acceptable, clay structured liquids have a number of disadvantages. Montmorillonite clays, even in the presence of stabilizing agents, are sensitive to ionic strength. They lose their liquid structuring efficiency at the high electrolyte levels normally present in autodish liquid detergents. Clays tend to collapse onto themselves, or flocculate under these conditions. If this collapse occurs to any large extend during prolonged storage, the liquid will lose its physical stability, suffer syneresis and/or settling of solids. Collection of solids at the bottom of the container can lead to the formation of paste-like plugs which are difficult to dispense.

Attapulgite clay particles suspended in liquids tend to scatter light. Any large amount of these clay particles will thus impart a muddy dull color to the liquid. Furthermore, clays, being insoluble minerals, can adversely affect glass appearance. Deposition of clay onto the surface of glassware has been known to lead to spotting and filming.

Another problem of suspended solids in prior art liquids is that they are subject to recrystallization during storage periods. Through a process of Ostwald ripening, the solids can redistribute themselves in terms of number and size of crystals. These changes can cause a drastic change in rheology of the liquid over time. Poor stability and/or cup retention result.

Many polymers are known for their thickening properties. Within the machine dishwashing art, polyacrylic acid type polymers have been included as an important component but not necessarily to function as a thickener. Thus, U.S. Pat. No. 3,579,455 (Sabatelli et al.) discusses what is evidently a powdered dishwashing detergent utilizing sodium polyacrylate as an anti-spotting/streaking agent and hardness precipitator. Polyacrylate has also been incorporated into thixotropic liquids that have been primarily thickened with powdered clay. GB Nos. 2 163 447A (Colarusso) and 2 164 350A (Lai et al.) contain such clay-sodium polyacrylate systems and suggest that the polymer provides improved protection to the overglaze layer of fine china. Less filming on glassware was also noted.

Use of polymers for gel-formation in liquid detergent compositions was suggested in U.S. Pat. No. 3,060,124 (Ginn). Apparently, cross-linked vinyl polymers are primarily suitable. Hydrolyzed polyacrylonitrile cross-linked with formaldehyde was found particularly effective at stabilizing the gels against separation. U.S. Pat. No. 4,228,048 (Tesdahl) illustrates the use of polyallyl sucrose cross-linked polyacrylates, commercially available under the trademark Carbopol ®, as a thickener for liquid cleaning and bleaching concentrates. Japanese Laid Open Patent Nos. 59-36198 (Kao Soap) and 59-36200 (Kao Soap) further illustrate the use of polyacrylate cross-linked with compounds such as allylated pentaerythritol. These thickened formulas are used to suspend water-insoluble abrasives such as silicone dioxide and aluminum oxide.

Although the aforementioned polymer systems do provide some measure of thickening and phase stabilization, they are frequently not fully adequate at such functions, especially where there is a high level of electrolyte present. Systems are required exhibiting improved stability against phase separation at high electrolyte level and having improved rheological properties. With regard to rheology, the composition must not substantially leak from the cup of an automatic dishwasher, but at the same time be sufficiently shearing to allow flow out of its container.

There has also been a search for more aesthetically pleasing product forms. Clay structurants cream the carrier liquid resulting in an opaque product. Many polymers also impart opaque properties. Clear compositions would, by contrast, be more aesthetically pleasing to the consumer.

Liquids including all those of the aforementioned art have another undesirable characteristic. Subsequent to pouring, the mouth of the pouring container will retain flow cut-off product droplets. Normally, these droplets will travel from the lip downward along the outside of the container. Consumers do not like the resulting mess. Some containers have been designed with special pour spouts to prevent this problem. The spouts are, however, quite expensive and not normally used for small-sized containers. It would therefore be desirable to obtain a product inherently having non-drip properties.

Accordingly, it is an object of the present invention to obtain a composition in gel form readily flowable from its container but, nevertheless, having rigidity when not subjected to shearing forces. With particular respect to automatic dishwashing compositions, it is an object of the present invention to provide a gel product that can readily be dispensed from its bottle but, once placed in a retaining cup of an automatic dishwasher will have sufficient thickness not to leak from the cup before dispensing.

Another object of the present invention is to provide a gel that is clear.

A further object of the present invention is to provide a gel cleaning composition pourable from a container similar to ordinary liquids but having a recoil elasticity rendering the composition dripless.

A further object of the present invention is to provide an automatic dishwashing composition in gel form having improved storage stability so as to avoid phase separation.

A still further object of the present invention is to provide an automatic dishwashing composition which does not require clay structurants.

Also an object of the present invention is to provide an automatic dishwashing composition having reduced spotting and filming with respect to glassware.

Finally, another object of the present invention is to provide a cleaning composition in gel form that may also be utilized in applications other than automatic dishwashing including those of fabric washing, fabric softening, bleaching, hard surface cleaning and similar functions.

These and other objects of the present invention will become apparent as further details are provided in the subsequent discussion and Examples.

SUMMARY OF THE INVENTION

An aqueous cleaning composition is provided in a gel form having a viscosity on a Haake Rotovisco RV-100 Viscometer at 25° C. under 5 sec$^{-1}$ shear of from about 1,000 to 20,000 cps and under 21 sec$^{-1}$ shear of from about 200 to 5,000 cps, a pH range from 11 to 13, and a steady state viscoelastic deformation compliance $J_e°$ greater than 0.01.

A preferred embodiment of the aforementioned aqueous cleaning gel composition is a material comprising from 0.1 to 10% of a thickener that is a cross-linked polycarboxylic polymer. Desirably, there should also be present from 0.01 to 10% of a trivalent metal containing material. Aluminum is the most suitable trivalent metal and aluminum oxide is the preferred material. Moreover, there may be present from 1 to 60% of a water-soluble structuring chelant selected from the salts of carbonate, pyrophosphate and mixtures thereof. Potassium carbonate, tetrapotassium pyrophosphate and mixtures of these salts are best selected as the structuring chelants. Clear, nearly transparent, properties are retained by the composition even in the presence of polymer thickener, trivalent metal containing material, and structuring chelant.

DETAILED DESCRIPTION OF THE INVENTION

The aqueous cleaning compositions of the present invention have several properties which are unusual and surprising. Unlike known gel compositions, the present material has an elastic nature rendering the material non-dripping. When tilting a container upright again after pouring, the discharging gel exhibits a memory, recoiling back into the container without leaving any drop of liquid around the container mouth. The effect is somewhat akin to the action of a yo-yo. Gel elasticity is believed to arise from strong intermolecular entwinning which does not seem to occur in other systems. A physical measure of this elasticity or recoil is $J_e°$, the steady state compliance value. $J_e°$ is derived from steady state viscoelastic deformation measurements performed through well known standard techniques (see J. Ferry, "Viscoelastic Properties of Polymers", Third Edition, John Wiley & Sons, New York, 1980). $J_e°$ reflects the elastic deformation and/or energy stored in the elastic components of a fluid during steady flow. This value identifies the extent to which a fluid rebounds when stress is removed. Rebounding or recoil is a property associated with visual perception of elasticity. The $J_e°$ value should be greater than about 0.01 meters$^2$/Newton, preferably greater than about 0.02 meter$^2$/Newton, and optimally between 0.02 and 0.10.

Gel compositions of this invention must also have acceptable flowability from a container but, when at rest, must be relatively non-flowing. The non-flowing property is important in such areas such as automatic dishwashing detergents. When such a detergent is placed in an automatic dishwashing dispenser cup, the detergent composition should have sufficient structural integrity not to rapidly flow out of the dispenser cup. Thus, gel compositions of this invention should possess under the minimum shear conditions of 5 sec$^{-1}$ at 25° C., a viscosity of from about 1,000 to 20,000 cps, preferably from about 1,500 to 10,000 cps, optimally between 3,000 and 7,000 cps. Under flow conditions represented by the shear rate of 21 sec$^{-1}$ at 25° C., the viscosity should range from about 200 to 5,000 cps, preferably from about 800 to 4,000 cps, optimally from 900 to 2500 cps. The aforementioned viscosities are measured on a Haake Rotovisco RV-100 Viscometer. A pH range for these liquids varies from about 11 to 13.

Another unusual property that certain embodiments of the present invention may possess is that of clarity or near transparency. The term "clear" as used in the specification is intended to connote its usual dictionary definition. Thus, a clear composition allows ready viewing of objects behind it. By contrast, a translucent composition although allowing light to pass through, causes light to be so scattered as by a very small portion of crystals or insolubles, that it will be impossible to clearly identify objects behind the translucent material. Within the context of this invention, the composition is deemed to be clear if the maximum transmittance of light through a sample 2 cm thick is at least 10%, preferably at least 20%, optimally greater than 50%. A gel is deemed translucent if the maximum transmittance of such light through the sample is between 5% and 10%. Finally, a gel is deemed opaque if the maximum transmittance of light is below 5%. This transmittance can easily be measured by placing a sample of the aforestated thickness in the light path probe of a Brinkmann PC 800, Colorimeter fitted with a 470 nm filter. Distilled water is considered a baseline for 100% transmittance.

In one embodiment of the present invention, it has been found that a gel with the aforedescribed unique recoil properties can be obtained by use of a cross-linked polycarboxylate polymer. Desirably, there should also be present a trivalent metal containing material. Moreover, there preferably should be present a structuring chelant.

Polycarboxylic thickening polymers in aqueous media are known to tolerate, without phase separation, modest electrolyte levels in such products as liquid automatic dishwashing detergents. Problems of phase separation will, however, occur when these modest electrolyte levels are substantially increased by the addition of further salts. Thus, according to the first embodiment, it has been found that certain cross-linked polycarboxylic polymers will impart a reasonably high viscosity to liquids even in the presence of high levels of salts.

Further work has indicated that high viscosity alone is insufficient for certain product systems. For instance, automatic dishwashing products require an adequate level of product retention within the cup of a dishwashing machine. For such product applications, it has been found desirable to include small amounts of aluminum containing compounds that will interact with the cross-linked polycarboxylic polymers to substantially improve product rheology.

Dependent upon the chosen polymer and aluminum containing compound, it may be desirable to also include a water-soluble structuring chelant. The matrix formed through the interaction of cross-linked polymer, aluminum compound and structuring chelant affords a salt tolerant gel unaffected by the presence of alkaline sources, builder salts and other soluble ionic species.

By the use of the aforedescribed matrix, it is possible to obtain a clear gel even in the presence of alkaline salts, builders, surfactants and other minor ingredients. The system provides for complete solubility of the foregoing components; the matrix is a highly suspending one. Thereby is achieved the additional benefit of eliminating suspended solids, and the attendant settling-separation problems. If desired, significant amounts of light dispersing solids may nevertheless be included in the matrix. Translucent or opaque gels would then result.

The polymeric thickener of the first embodiment of the invention is a polycarboxylic polymer that has been interpolymerized with a multi-vinyl or multi-allylic functionalized cross-linking agent. Preferably, the polycarboxylic polymer is interpolymerized with a polyalkenyl polyether of a polyhydric compound. The polyhydric compound should have at least 4 carbons and 3 hydroxy groups. These thickeners are described in U.S. Pat. Nos. 2,798,053 and 4,130,501, both of which are herein incorporated by reference. More specifically the thickeners are water dispersible copolymers of an alpha-beta monoolefinically unsaturated lower aliphatic carboxylic acid cross-linked with a polyether of a polyol. The polyol may be selected from the group consisting of oligosaccharides, reduced derivatives thereof in which the carbonyl group is converted to an alcohol group, and pentaerythritol. The hydroxy groups of said polyol are etherified with allyl groups, said polyol having at least two allyl groups per polyol molecule. A suitable copolymer is one of acrylic acid with low percentages (0.71 to 1.5%) poly allyl sucrose.

Molecular weights of the cross-linked polymer may range from about 500,000 up to 10,000,000, preferably between 500,000 and 2,000,000, optimally about 1,250,000. Examples of commercially available cross-linked polymers based upon allyl sucrose modified polyacrylic acid are the Carbopol ® resins manufactured by the B. F. Goodrich Chemical Company. These materials include Carbopol 941 ® (m.w. 1,250,000), Carbopol 934 ® (m.w. 3,000,000) and Carbopol 940 ® (m.w. 4,000,000). Most preferred is Carbopol 941 ® which gives the best structuring and clarity.

The polymeric thickener of this invention may be present in an amount from about 0.1 to about 10%, preferably from about 0.5 to 2% optimally between about 0.7 and 1.5% by weight of the composition.

In conjunction with the polymeric thickener, there may be present a co-structurant such as a trivalent metal containing material. Most effective are those materials containing aluminum, especially aluminum salts or aluminum oxides. Among the inorganic aluminum salts that have been found useful are those with counterions selected from sulfate, chloride, phosphate, nitrate, chlorhydroxide, bromide, carbonate and fluoroborate. Alumina is however the most effective source of aluminum. A most preferred form of this material is boehmite, a crystalline phase of aluminum oxyhydroxide. Especially desirable is a semi-crystalline phase commonly referred to as pseudoboehmite. Aluminosilicates were found not to be effective co-structurants and, for purposes of this invention, are excluded as the trivalent metal ion source. Of course, aluminosilicates (e.g. zeolites) might be present for other purposes, such as for calcium hardness sequestration, in the gel compositions, especially where clarity of the fully formulated product is unnecessary.

Trivalent metal containing material may be present in an amount from 0.01 up to 10%, preferably from about 0.1 to about 4%, optimally from about 0.1 to 2% by weight of the composition.

A third desirable element of the gel composition is a water-soluble structuring chelant. Particularly suitable are salts of carbonate, pyrophosphate and mixtures of these two materials. For purposes of product clarity, it is preferable to select potassium as the counterion to the carbonate and/or pyrophosphate. Small amounts of sodium may, however, be tolerated. Thus, the molar ratio of potassium to sodium ion should preferably be greater than 1:1, and optimally greater than 4:1. Under situations where potassium carbonate and potassium pyrophosphate are both present, the relative ratio of these chelants will be from 1:10 to 10:1, preferably from 1:4 to 4:1, optimally about 1:4 to 1:1.5. The amount of chelant may range anywhere from about 1% up to about 60%, preferably between about 15 and 35%, optimally between about 25 and 30% by weight of the composition.

When the gel composition is used as an automatic dishwashing formulation, it will normally also contain an oxidizing agent. Traditionally, liquid dishwashing compositions have for this purpose utilized sodium hypochlorite because it is inexpensive. Other oxidizing agents may, however, be employed. For instance, it is also possible to utilize heterocyclic N-bromo and N-chloro imides such as trichlorocyanuric, tribromocyanuric, dibromo and dichlorocyanuric acids, and salts thereof with water solubilizing cations such as potassium and sodium. An example of a hydrated dichlorocyanurate acid is Clearon CDB 56, a product manufactured by the Olin Corporation. The oxidizing material will be present in the mixture from about 0.1 to 10%, with the most preferred range being from 0.1 to 2% by weight. Preferred concentrations will provide about 0.2 to about 1.5 weight % available chlorine.

Automatic dishwashing detergent compositions based upon this invention will also contain sodium or potassium silicate. This material is employed as a cleaning ingredient, source of alkalinity, metal corrosion inhibitor, and protector of glaze on china tableware. Especially effective is sodium silicate having a ratio of $SiO_2$:$Na_2O$ from about 1.0 to about 3.3, preferably from about 2 to about 3.2. The silicate may be used in the form of an aqueous liquor or a solid. It will be present from about 0.1 to 25%, more preferably from about 5 to 10% by weight of the composition.

Surfactants are desirably part of the aforementioned compositions. These surfactants should be of the low-foaming type; foam interferes with the dishwasher cleaning action. Suitable surfactants may be selected from nonionic, anionic and amphoteric types and mixtures thereof. Nonionic surfactants can be broadly defined as compounds produced by the condensation of alkylene oxide groups with an organic hydrophobic material which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Illustrative, but not limiting examples, of the various chemical types as suitable nonionic surfactants include:

(a) polyoxyethylene or polyoxypropylene condensates of aliphatic carboxylic acids, whether linear- or branched-chain and unsaturated or saturated, containing from about 8 to about 18 carbon atoms in the aliphatic chain and incorporating from 5 to about 50 ethylene oxide and/or propylene oxide units. Suitable carboxylic acids include "coconut" fatty acids (derived from coconut oil) which contain an average of about 12 carbon atoms, "tallow" fatty acids (derived from tallow-class fats) which contain an average of about 18 carbon atoms, palmitic acid, myristic acid, stearic acid and lauric acid.

(b) polyoxyethylene or polyoxypropylene condensates of aliphatic alcohols, whether linear- or branched-chain and unsaturated or saturated, containing from about 6 to about 24 carbon atoms and incorporating from about 5 to about 50 ethylene oxide and/or propylene oxide units. Suitable alcohols include the "coconut" fatty alcohol, "tallow" fatty alcohol, lauryl alcohol, myristyl alcohol and oleyl alcohol. Particularly preferred nonionic surfactant compounds in this category are the "Neodol" type products, a registered trademark of the Shell Chemical Company.

Included within this category are nonionic surfactants having the formula:

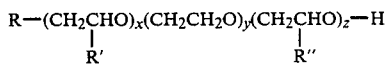

wherein R is a linear, alkyl hydrocarbon having an average of 6 to 10 carbon atoms, R' and R" are each linear alkyl hydrocarbons of about 1 to 4 carbon atoms, x is an integer from 1 to 6, y is an integer from 4 to 15 and z is an integer from 4 to 25. A particularly preferred example of this category is Poly-Tergent SLF-18, a registered trademark of the Olin Corporation, New Haven, Conn. Poly-Tergent SLF-18 has a composition of the above formula where R is a $C_6$–$C_{10}$ linear alkyl mixture, R' and R" are methyl, x averages 3, y averages 12, and z averages 16.

(c) polyoxyethylene or polyoxypropylene condensates of alkyl phenols, whether linear- or branched-chain and unsaturated or saturated, containing from about 6 to about 12 carbon atoms and incorporating from about 5 to about 25 moles of ethylene oxide and/or propylene oxide.

(d) polyoxyethylene derivatives of sorbitan mono-, di-, and tri-fatty acid esters wherein the fatty acid component has between 12 and 24 carbon atoms. The preferred polyoxyethylene derivatives are of sorbitan monolaurate, sorbitan trilaurate, sorbitan monopalmitate, sorbitan tripalmitate, sorbitan monostearate, sorbitan monoisostearate, sorbitan tristearate, sorbitan monooleate, and sorbitan trioleate. The polyoxyethylene chains may contain between about 4 and 30 ethylene oxide units, preferably about 20. The sorbitan ester derivatives contain 1, 2 or 3 polyoxyethylene chains dependent upon whether they are mono-, di- or tri-acid esters.

(e) polyoxyethylene-polyoxypropylene block copolymers having the formula:

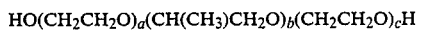

wherein a, b and c are integers reflecting the respective polyethylene oxide and polypropylene oxide blocks of said polymer. The polyoxyethylene component of the block polymer constitutes at least about 40% of the block polymer. The material preferably has a molecular weight of between about 2,000 and 10,000, more preferably from about 3,000 to about 6,000. These materials are well known in the art. They are available under the trademark "Pluronics", a product of the BASF-Wyandotte Corporation.

Low foaming anionic surfactants are also very useful for this invention, especially when combined with effective defoaming materials. Anionics are desirable because they are more stable towards hypochlorite than the nonionic type. Illustrative of this category are alkyl diphenyloxide sulfonate, alkyl naphthalene sulfonate, sodium 2-acetamidohexadecane sulfonate and nonionic alkoxylates having a sodium alkylene carboxylate moiety linked to a terminal hydroxy group of the nonionic through an ether bond.

Surfactants will usually be present in an amount from about 0.1 to 25%, preferably from about 0.15 to 5%, optimally from about 0.2 to 3% by weight of the composition.

Defoaming of the wash may be accomplished by the presence of any of a number of commercially available defoaming agents. These agents may be of the general type of slightly soluble alkyl carboxylates, alkyl phosphates, hydrocarbon waxes, hydrophobic silicas, silicone defoamers, or many others. In addition to being an effective defoamer, the species must be stable to hypochlorite. The defoamer will optionally be present in the composition from about 0.05% to 5%, preferably from about 0.1 to 1%, and most preferably from about 0.1 to 0.5% by weight of the composition.

Amounts of water present in the liquid compositions should neither be so high as to produce unduly low viscosity and fluidity, nor so low as to produce unduly high viscosity and low flowability, thixotropic properties in either case being diminished or destroyed. Water will generally be present in an amount ranging from about 25 to 80%, preferably from about 45 to 75%, optimally from about 55 to 65% by weight of the composition.

An alkali metal hydroxide will be used as an alkaline source and as a means to boost the pH to stabilize hypochlorite. Although small amounts of sodium hydroxide may be utilized, this material is desirably excluded in favor of potassium hydroxide. The potassium hydroxide may be added in the form of an aqueous liquor or as a solid. Amounts of potassium hydroxide will range from about 0.1 to 10%, preferably about 0.5 to 5%, and optimally about 1 to 2% by weight of the composition.

Minor amounts of various other adjuvants may be present in the gel composition. Thus, the compositions may include perfumes, flow control agents, soil suspending agents, antiredeposition agents, anti-tarnish agents, enzymes and other functional additives.

Although the gels of this invention have been specifically designed for automatic dishwashing compositions and the foregoing specification has detailed such formulated products, it must be emphasized that the base gel structure can be utilized for other purposes. Thus, it is envisioned that the gel composition of this invention may be useful in products such as fabric washing formulations, hand dishwashing liquids, toilet bowl scrubs, pot/pan cleaners, fabric softeners, denture cleaners and even shampoos.

The following examples will more fully illustrate the embodiments of this invention. All parts, percentages and proportions referred to herein and in the appended claims are by weight unless otherwise indicated.

EXAMPLES 1-4

One embodiment illustrative of the present invention is the formula outlined under Examples 2-4. These Examples were formulated to investigate changes in the concentration of the aluminum containing material, Catapal D alumina.

| Component | Examples | | | |
|---|---|---|---|---|
| | 1 | 2 | 3 | 4 |
| Tetrapotassium pyrophosphate | 19.0 | 19.0 | 19.0 | 19.0 |
| Britesil H2O (sodium silicate) | 7.5 | 7.5 | 7.5 | 7.5 |
| Potassium carbonate | 6.0 | 6.0 | 6.0 | 6.0 |
| Sodium tripolyphosphate | 1.0 | 1.0 | 1.0 | 1.0 |
| Potassium hydroxide | 1.0 | 1.0 | 1.0 | 1.0 |
| Carbopol 941 ® | 1.0 | 1.0 | 1.0 | 1.0 |
| Catapal D Alumina | — | 0.05 | 0.1 | 0.2 |
| Water | to 100 | to 100 | to 100 | to 100 |
| Cup retention (viscosity) | | | | |
| at 5 sec$^{-1}$ shear (cps) | 1343 | 3571 | 6193 | 6493 |
| at 21 sec$^{-1}$ shear (cps) | 711 | 996 | 1956 | 2223 |

Example 1 is a formulation containing Carbopol 941 ® and the structuring chelants, potassium carbonate and potassium pyrophosphate. Alumina was absent from this formulation. Pourability of the Examples was evaluated by measuring the viscosity under high shear conditions (i.e. 21 sec$^{-1}$). Pourability is considered adequate if the value under high shear at 25° C. is no greater than 5,000 cps. On the other hand, the "at rest" or cup retention viscosity property was measured at low shear (5 sec$^{-1}$) at 25° C. Here a value no lower than about 1,500, preferably 3,000 cps is needed.

Under high shear, Example 1 was measured to have a value of 711 cps which indicated satisfactory pourability. However, the "at rest" viscosity value of 1343 cps was very poor. The formula of Example 1 would not adequately be retained by a dishwasher dispenser cup. By contrast, Example 2 had an adequate pourability of 996 cps and a very substantial viscosity of 3,571 cps when "at rest" in the dispenser cup. It is to be noted when using Catapal D Alumina, a plateau in the "at rest" or storage viscosity occurs at about 0.1 wt. %.

EXAMPLE 5

Elastic rebound or recoil properties are discussed in this Example. Viscoelasticity properties were measured using a Carrimed Control Stress Rheometer type 5010 operated in the Creep Mode. A cone-and-plate geometry was employed. Cone radius was 3 centimeters and cone angle was 2°. In the Creep Mode, a constant stress is applied to the sample during which sample deformation is traced over a period of time. This deformation typically has two components for a viscoelastic fluid. The viscous component increases linearly with time while the viscoelastic component rises at a rate which decreases with time, eventually reaching the steady state value. The steady state viscoelastic deformation can be used to define the steady state compliance $J_e^\circ$. Tabulated below are the results of $J_e^\circ$ measurements on a series of aqueous liquids or gels having various thixotropic components.

| Sample | Component | $J_e^\circ$ |
|---|---|---|
| 1 | Carbopol 941 ® | 0.058 |
| 2 | Carbopol 941 ® Catapal D Alumina | 0.038 |
| 3 | Carbopol 941 ® Catapal D Alumina Tetrapotassium Pyrophosphate | 0.025 |
| 4 | Linear Sodium Polyacrylate Catapal D Alumina Tetrapotassium Pyrophosphate | 0.000 |
| 5 | Commercial Clay-Based Automatic | 0.0025 |

| Sample | Component | $J_e°$ |
|--------|-----------|--------|
| | Dishwashing Liquid | |

From the results listed in the Table, it is evident that non-crosslinked linear sodium polyacrylate in the context of Catapal D Alumina and tetrapotassium pyrophosphate does not possess rebound as is the case with the formula using Carbopol 941 ®. Cross-linking is thus quite important with respect to the polyacrylate polymer. Commercial clay-based automatic dishwashing liquids or gels also do not have any significant amount of rebound; they are not dripless in contrast to Sample 3.

EXAMPLES 6–9

Illustrated herein is the effect of varying the concentration of Carbopol 941 ®. The "at rest" or storage viscosity substantially increases around 0.7% Carbopol 941 ® to achieve an acceptable thickness. Although the pour viscosity under shear also increases as polymer increases, this viscosity still remains within an acceptable level.

| Component | Examples | | | |
|-----------|------|------|------|------|
| | 6 | 7 | 8 | 9 |
| Tetrapotassium pyrophosphate | 19.0 | 19.0 | 19.0 | 19.0 |
| Britesil H2O (sodium silicate) | 7.5 | 7.5 | 7.5 | 7.5 |
| Potassium carbonate | 6.0 | 6.0 | 6.0 | 6.0 |
| Sodium tripolyphosphate | 1.0 | 1.0 | 1.0 | 1.0 |
| Potassium hydroxide | 1.0 | 1 0 | 1.0 | 1.0 |
| Catapal D Alumina | 0.1 | 0.1 | 0.1 | 0.1 |
| Carbopol 941 ® | 0.4 | 0.6 | 0.8 | 1.0 |
| Water | to 100 | to 100 | to 100 | to 100 |
| Cup retention (viscosity) | | | | |
| at 5 sec$^{-1}$ shear (cps) | 744 | 1041 | 4315 | 6343 |
| at 21 sec$^{-1}$ shear (cps) | 265 | 531 | 2373 | 2089 |

EXAMPLE 10

This Example investigates the effect of various polymeric thickeners on phase stability and clarity of the formulation. A base composition was prepared having the following components.

| Base Composition | |
|---|---|
| Component | Weight % |
| Tetrapotassium Pyrophosphate | 19.0 |
| Britesil H2O (sodium silicate) | 7.5 |
| Potassium Carbonate | 6 0 |
| Sodium Tripolyphosphate | 1.0 |
| Potassium Hydroxide | 1.0 |
| Catapal D Alumina | 0.1 |
| Polymeric Thickener | * |
| Water | to 100 |

Within the above base composition were incorporated the polymers as outlined in the table below.

| Polymeric Thickener | Polymer Identification | Weight % | Stability | % Transmittance |
|---|---|---|---|---|
| Hercules CMC 7H4F | Sodium Carboxymethyl Cellulose | 1.0 | Unacceptable | nil |
| Alco EXP 1098-5 | Hydrophobically Modified Polyacrylate | 1.2 | Unacceptable | nil |
| Alcogum SL-60 | Polyacrylic Acid Emulsion | 1.0 | Unacceptable | nil |
| Alcosperse 175 | Polyacrylic Acid (m.w. 20,000) | 1.0 | Unacceptable | nil |
| National Starch Polymer | Polyacrylic Acid (m.w. 5000) | 1.0 | Unacceptable | nil |
| Carbopol 907 ® | Cross-Linked Polyacrylic Acid (m.w. 450,000) | 2.4 | Borderline | 10 |
| Carbopol 934 ® | Cross-Linked Polyacrylic Acid (m.w. 3,000,000) | 1.0 | Borderline | 11 |
| Carbopol 940 ® | Cross-Linked Polyacrylic Acid (m.w. 4,000,000) | 1.0 | Borderline | — |
| Carbopol 941 ® | Cross-Linked Polyacrylic Acid (m.w. 1,250,000) | 1.0 | Excellent | 60 |

All the non-crosslinked polymers listed in the table either precipitated in some way or phase separated from the electrolyte solution. All were non-homogeneous. Fully clear gels were also not obtainable. Carbopol 907 ®, 934 ® and 940 ® were not as clear as Carbopol 941 ® and were borderline with respect to phase stability.

EXAMPLE 11

Herein is presented the investigation of various co-structurants and their effect upon clarity of the gel.

| Co-Structurant | Viscosity (cps) | | Concentration Weight % | Fresh Appearance |
|---|---|---|---|---|
| | 5 sec$^{-1}$ | 21 sec$^{-1}$ | | |
| Catapal D Alumina (pseudoboehmite) | 7,942 | 3,118 | 0.1 | Clear |
| MgSO4 | 5,450 | 1,351 | 0.236 | Clear |
| Cr2(SO4)3.9H2O | 11,939 | 3,407 | 0.437 | Opaque |
| Cr2O3 | 7,691 | 2,809 | 0.149 | Opaque |
| Fe2O3 | 4,180 | 1,692 | 0.156 | Opaque |
| Fe2(SO4)3.9H2O | 6,019 | 2,207 | 0.553 | Opaque |
| CaCl2.5H2O | 5,751 | 1,438 | 0.288 | Opaque |
| CuSO4.5H2O | 8,652 | 2,505 | 0.313 | Translucent |
| ZnSO4.7H2O | 7,524 | 1,739 | 0.563 | Opaque |
| K2SO4 | 2,082 | 752 | 0.17 | Transparent |

Co-structuring salts as listed in the table were incorporated into a base composition identical to that used with Example 10 and having included therein 1% of Carbopol 941 ®. With the exception of Catapal D Alumina, all the co-structurants listed above formed precipitate over time. Also, none of the above salts gave the degree of clarity provided by alumina.

EXAMPLE 12

The effects of various chelant/electrolyte combinations have also been investigated. A base formula as outlined below was utilized into which were incorporated various sodium and potassium compounds.

| Base Composition | |
|---|---|
| Component | Grams |
| Water | 34.5 |
| Potassium Hydroxide | 1.0 |
| Catapal D Alumina | 0.1 |
| Chelant/Electrolyte | * |
| Carbopol 941 ® | 1.0 |

| | | Viscosity (cps) | |
|---|---|---|---|
| Chelant/Electrolyte | Grams | 5 sec$^{-1}$ | 21 sec$^{-1}$ |
| Potassium nitrate | 20.0 | 3750 | 1607 |
| Potassium sulfate | 10.0 | 4875 | 1518 |
| Potassium tripolyphosphate | 15.0 | 3750 | 1250 |
| Sodium citrate | 10.0 | 1500 | 625 |
| Tetrasodium EDTA | 10.0 | 1012 | 919 |
| Dequest 2066 ® | 15.0 | 2625 | 1071 |
| Potassium chloride | 15.0 | 1275 | 677 |
| Potassium carbonate | 15.0 | 13125 | 4464 |
| Tetrapotassium pyrophosphate | 5.0 | 3348 | 1275 |
| Tetrapotassium pyrophosphate | 10.0 | 5691 | 1594 |
| Tetrapotassium pyrophosphate | 15.0 | 6026 | 1913 |
| Tetrapotassium pyrophosphate | 19.0 | 15750 | 5536 |

From the table, it is evident that potassium carbonate has a substantially greater viscosity increasing effect than an equivalent weight of potassium chloride, potassium nitrate or potassium tripolyphosphate. Tetrapotassium pyrophosphate is also seen to have a very substantial viscosity building property.

EXAMPLES 13-16

Illustrated here is the effect of nonionic surfactants upon glass cleaning performance. Ten (10) dinner plates and ten (10) clean glass tumblers were placed in a Kenmore dishwasher. Forty (40) grams of a 4:1 mixture of margarine and powdered milk were placed in the dishwasher. Plates and glasses were then washed with test liquid or control products. Dishwasher dispenser cups were filled with test liquid or control product at equal volume (approximately 40 grams of granular control versus 60 grams of test liquid). After each cycle, glasses were visually inspected and then placed in another machine. Each glass was numerically rated for spotting and filming on a scale of 0 to 4 (0=best; 4=worst). Values for each glass in each of four runs were averaged together for an overall rating.

The base composition of Example 10 was utilized and further included 1% Carbopol 940 ®, 1.75% sodium dichloroisocyanurate, and 2% surfactant. Examples 13 and 15 incorporated Poly-Tergent SLF-18 ® as the nonionic surfactant. Example 15, unlike Example 13 did not contain sodium dichloroisocyanurate. Example 14 utilized AKYPO LA 294, a nonionic surfactant sold by BASF-Wyandotte Corp. and structurally identified as a phenol ethoxylated with 3 moles ethylene oxide and end-capped with sodium acetate. Example 16 contained only the base composition without surfactant. The control was a commercial opaque thixotropic liquid formulated with a clay thickener.

| | Performance | | |
|---|---|---|---|
| Example | Surfactant | Spotting | Filming |
| 13 | Poly-Tergent SLF-18 ® | 0.25 | 0.75 |
| 14 | AKYPO LA 294 ® | 2.8 | 1.9 |
| 15 | Poly-Tergent SLF-18 ® | 2.2 | 0.7 |
| 16 | None | 1.2 | 1.8 |
| Control (Commercial ADD Liquid) | — | 2.3 | 1.3 |
| Control (Commercial ADD Powder) | — | 0.4 | 0.5 |

From the performance table, it is seen that Example 13 with Poly-Tergent SLF-18 ® provided spotting and filming results superior to that of other liquids tested and to the control commercial liquid. The formulation was also performance competitive with a typical commercial powder formulation.

The foregoing description and examples illustrate selected embodiments of the present invention. In light thereof, variations and modifications will be suggested to one skilled in the art, all of which are within the spirit and purview of this invention.

What is claimed is:

1. A cleaning composition in gel form having a viscosity on a Haake Rotovisco RV-100 Viscometer at 25° C. under 5 sec$^{-1}$ shear of from about 1,000 to 20,000 cps and under 21 sec$^{-1}$ shear of from about 200 to 5,000 cps, a pH range from 11 to 13, a steady state viscoelastic deformation compliance $J_e°$ value greater than 0.01, and a light transmittance not lower than 10% through a sample 2 cm thick, said composition comprising:
   (i) from 0.1 to 10% of a thickener that is a cross-linked polycarboxylic polymer; and
   (ii) from 0.01 to 2% of alumina.

2. A composition according to claim 1 wherein the value for said viscoelastic deformation compliance $J_e°$ ranges from about 0.02 to 0.1.

3. A composition according to claim 1 wherein the value of said viscoelastic deformation compliance $J_e°$ ranges from about 0.025 to 0.06.

4. A composition according to claim 1 wherein the viscosity of the composition at 5 sec$^{-1}$ and 25° C. ranges from about 1,500 to 10,000 cps.

5. A composition according to claim 1, wherein the light transmittance is greater than 50%.

6. A composition according to claim 1 further comprising from about 0.1 to 10% by weight of a chlorine releasing oxidizing agent.

7. A composition according to claim 1 wherein the alumina is a semi-crystalline phase boehmite known as pseudo boehmite.

8. A composition according to claim 1 wherein the trivalent metal containing material is present in an amount from about 0.1 to about 2% by weight of the composition.

9. A composition according to claim 1 further comprising from about 0.1 to about 25% of a surfactant.

10. A composition according to claim 9 wherein said surfactant is selected from the group consisting of nonionic, anionic, cationic, amphoteric, surface active compounds and mixtures thereof.

11. A composition according to claim 10 wherein said nonionic surfactant is a $C_6$–$C_{10}$ alkanol alkoxylated with a mixture of ethylene oxide and propylene oxide.

12. A composition according to claim 1 further comprising from 1 to 60% of a water-soluble structuring chelant selected from the salts of carbonate, pyrophosphate and mixtures thereof.

13. A composition according to claim 12 wherein the structuring chelant is present in an amount from about 5% to about 40% by weight of the composition.

14. A composition according to claim 12 wherein the chelant is selected from the group consisting of potassium carbonate, tetrapotassium pyrophosphate and mixtures thereof.

15. A composition according to claim 14 wherein potassium carbonate and tetrapotassium pyrophosphate are present together in a ratio of from 1:10 to 10:1.

16. A composition according to claim 15 wherein the ratio ranges from about 1:4 to 4:1.

17. A composition according to claim 1 wherein said polycarboxylic polymer is interpolymerized with a polyalkenyl polyether of a polyhydric alcohol.

18. A composition according to claim 17 wherein the polyhydric compound has at least 4 carbons and 3 hydroxy groups.

19. A composition according to claim 17 wherein the interpolymerized polycarboxylic polymer is present in an amount from about 0.5 to 2% by weight of the composition.

20. A composition according to claim 17 wherein the carboxylic polymer is a copolymer of an alpha-beta monoolefinically unsaturated lower aliphatic carboxylic acid cross-linked with a polyether of a polyol.

21. A composition according to claim 20 wherein the molecular weight of the polymeric thickener ranges from about 500,000 up to 10,000,000.

22. A composition according to claim 20 wherein the molecular weight ranges from about 500,000 to 2,000,000.

23. A composition according to claim 20 wherein the polyol may be selected from the group consisting of oligosaccharides, reduced derivatives thereof in which the carbonyl group is converted to an alcohol group, and pentaerythritol.

24. A composition according to claim 23 wherein hydroxyl groups of said polyol have been etherified with at least two allyl groups per polyol molecule.

* * * * *